United States Patent [19]

Ensminger et al.

[11] Patent Number: 5,256,146
[45] Date of Patent: Oct. 26, 1993

[54] VASCULAR CATHETERIZATION SYSTEM WITH CATHETER ANCHORING FEATURE

[75] Inventors: William D. Ensminger, 2770 Parkridge Dr.; James C. Andrews, 3568 River Pines; James A. Knol, 1059 Hasper, all of Ann Arbor, Mich. 48103

[73] Assignees: W. D. Ensminger; J. C. Andrews; J. A. Knol, all of Ann Arbor, Mich.

[21] Appl. No.: 775,045

[22] Filed: Oct. 11, 1991

[51] Int. Cl.⁵ .................................... A61M 29/00
[52] U.S. Cl. ................................. 604/104; 604/106; 604/280; 606/198
[58] Field of Search ............ 606/108, 191, 198, 200; 604/104–107, 280–281, 174, 175; 623/1, 12, 13; 128/DIG. 26

[56] References Cited

U.S. PATENT DOCUMENTS

| | | |
|---|---|---|
| 4,114,618 | 9/1978 | Vargas . |
| 4,419,094 | 12/1983 | Patel . |
| 4,488,877 | 12/1984 | Klein et al. . |
| 4,643,184 | 2/1987 | Mobin-Uddin ............. 606/198 X |
| 4,650,472 | 3/1987 | Bates . |
| 4,706,671 | 11/1987 | Weinrib ..................... 604/104 X |
| 4,737,141 | 4/1988 | Spits ................................ 604/28 |
| 4,747,840 | 5/1988 | Ladika et al. . |
| 4,768,507 | 9/1988 | Fischell et al. . |
| 4,813,925 | 3/1989 | Anderson, Jr. et al. . |
| 4,874,360 | 10/1989 | Goldberg et al. . |
| 4,887,996 | 12/1989 | Bengmark . |
| 4,909,781 | 3/1990 | Husted . |
| 4,909,789 | 3/1990 | Taguchi et al. ............... 604/107 |
| 4,950,258 | 8/1990 | Kawai et al. . |
| 4,957,479 | 9/1990 | Roemer . |
| 4,986,814 | 1/1991 | Burney et al. . |
| 4,994,069 | 2/1991 | Ritchart et al. ............... 606/191 |
| 4,997,435 | 3/1991 | Demeter ...................... 606/127 |
| 4,998,916 | 3/1991 | Hammerslag et al. . |
| 5,147,379 | 9/1992 | Sabbaghian et al. ......... 606/206 |
| 5,152,777 | 10/1992 | Goldberg et al. ............ 606/200 |

Primary Examiner—C. Fred Rosenbaum
Assistant Examiner—Corrine Maglione
Attorney, Agent, or Firm—Harness, Dickey & Pierce

[57] ABSTRACT

A patient implantable vascular catheterization system incorporating an anchoring element for maintaining the tip of an implanted catheter at a desired position within a blood vessel. The anchoring element comprises a deformable element such as a coiled wire or one or more expandable legs. The anchoring element is caused to assume a streamlined or compressed condition through placing it within an introducer catheter to facilitate placement or removal of the implanted catheter. Once positioned, the introducer catheter is retracted allowing the anchoring element to expand into engagement with the blood vessel. A material to induce occlusion of the blood vessel through clotting can be incorporated into the anchoring element.

16 Claims, 3 Drawing Sheets

VASCULAR CATHETERIZATION SYSTEM WITH CATHETER ANCHORING FEATURE

BACKGROUND AND SUMMARY OF THE INVENTION

This invention relates to patient vascular catheterization and particularly to a catheterization system incorporating an anchoring feature for supporting a catheter tip within a blood vessel.

In various interventional medical procedures it is desirable to place a catheter within a patient's blood vessel for purposes of infusion of drugs or fluids, or for withdrawing blood. In some cases it is desirable to maintain an implanted catheter within the patient for a prolonged period of time, for example, for regional chemotherapy.

Often, implanted vascular catheters are used with so-called "infusion ports" which are placed subcutaneously and connected to an implanted catheter. In the past such infusion ports typically featured a compressed rubber septum which is penetrated by a hypodermic needle to provide fluid transfer with the implanted catheter. The present applicants are the inventors of a new generation of implantable infusion ports which do not rely on a compressed rubber septum, but instead use an articulating catheter valve. Examples of such devices are found in the following U.S. patent applications which are hereby incorporated by reference: Ser. No. 487,541, filed on Mar. 1, 1990 entitled; Cath-Link Vascular Access Port, Ser. No. 539,793, filed on Jun. 18, 1990 entitled; Implantable Infusion Device, and Ser. No. 654,661, filed on Feb. 15, 1991 entitled; Implantable Infusion Device. These new generation infusion ports broadly expand the access which the clinician has to an implanted catheter, enabling external catheters, guide wires, optical fibers, etc. to be placed into the implanted catheter.

While present techniques for implanting catheters within a patient's vascular tract are extremely useful for various procedures, they have significant limitations. The types of standard implanted catheters inserted by angiographic or surgical procedures tend to move about after implantation, which may result in dislodgement from the desired position. Such movement can also lead to the catheter tip perforating the blood vessel wall. As an alternative, in some circumstances catheters can be surgically implanted and anchored for maintaining their positions. Surgical catheter placement and tip fixation, however, involves hospitalization and major surgery.

As one means of anchoring the tip of a catheter within a patient, catheters having a preformed curled configuration have been employed. Such a catheter is temporarily straightened through the use of a semi-rigid guide wire or trocar which is passed through the lumen of the catheter. While such approaches have been successfully implemented for placement of catheters within the urinary bladder, abdominal cavity or stomach, they are impractical for use for anchoring a catheter within a blood vessel. The small diameter of blood vessels necessarily dictates an extremely small diameter catheter to enable the catheter to assume a curled configuration within the blood vessel. Such catheters would have poor flow rate capacities. Moreover, such a coiled configuration would predispose to clotting and then blockage of blood flow through the blood vessel, which is undesirable in most instances.

In accordance with the present invention, various anchoring elements are described for maintaining an implanted catheter tip at a desired position for prolonged periods of time. Each of the embodiments of this invention includes an anchoring element which is formed such that, in its free state, it expands to engage the inside wall of a blood vessel to mechanically link the implanted catheter tip to the blood vessel. Insertion, and in some cases removal of the catheter, is provided by retracting or deforming the anchoring element temporarily by using an introducer catheter which forms the anchoring element to a streamlined configuration, enabling it to be moved along within the vessel. In accordance with one embodiment, a helical coiled wire is used as the anchoring element and is straightened for implantation by pulling the coil inside an introducer catheter. In another embodiment, an anchoring element is employed having at least one expanding resilient leg which is retracted when the anchoring element is pulled inside the introducer catheter. Further described are systems for intentionally causing the anchoring element to occlude a blood vessel by generating a localized clot.

Additional benefits and advantages of the present invention will become apparent to those skilled in the art to which this invention relates from the subsequent description of the preferred embodiments and the appended claims, taken in conjunction with the accompanying drawings.

oriented from the perspective of a patient lying face down with their head downward) in which the common hepatic artery through which the system is introduced is intentionally occluded.

Figure 9:
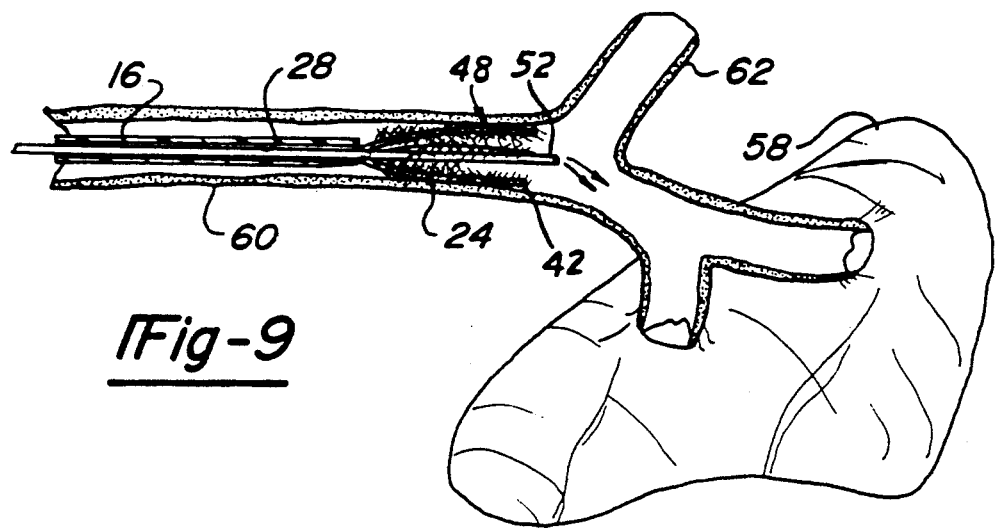
FIG. 9 is a pictorial view of the catheterization system of FIG. 8 shown being used for infusion within a human liver shown in a posterior-caudad position (i.e.
Figure 10:
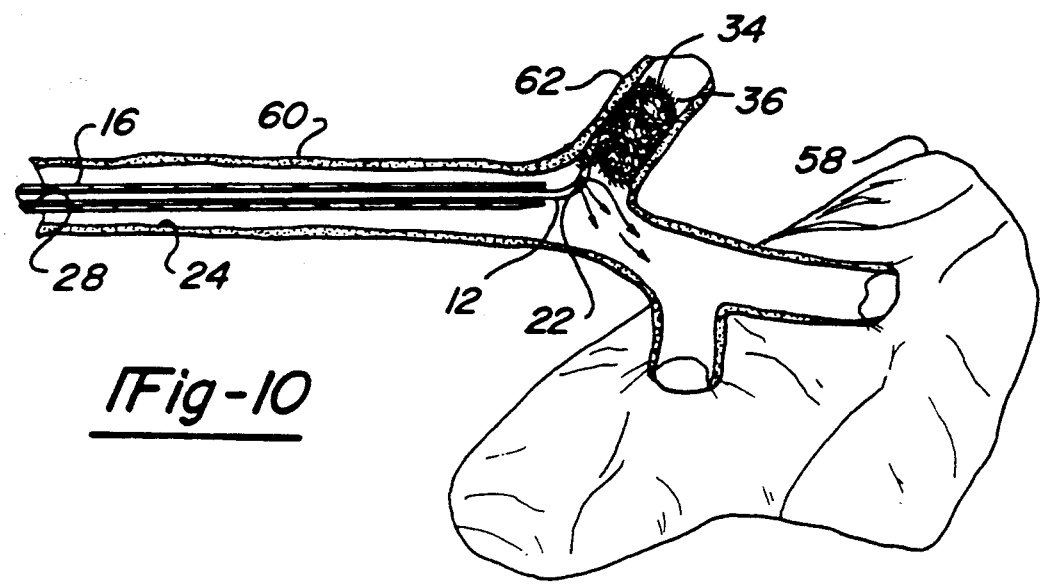

FIG. 10 is a pictorial view similar to FIG. 9 in orientation but showing the embodiment of this invention shown in FIG. 5 again for providing treatment of a patient's liver shown in a posterior-caudad position but showing the gastroduodenal artery being intentionally occluded.

DETAILED DESCRIPTION OF THE INVENTION

An implantable catheterization system in accordance with the first embodiment of this invention is shown in FIGS. 1 through 4 and is generally designated by reference number 10. Catheterization system 10 principally comprises infusion catheter 12, anchoring wire element 14, introducer catheter 16, and guide wire 18. The elements of system 10 are broken away in the Figures to enhance the clarity of their illustration.

Infusion catheter 12 is a generally conventional small caliber catheter, made for example, of implantable silicone rubber. Infusion catheter 12 has at least a single lumen 20 for the transport of fluids or for permitting access by a fiber optic cable, guide wire or other filament. Side port 22 provides penetration of lumen 20 to the interior of the patient's blood vessel, designated by reference number 24. As shown, catheter 12 has a cross-sectional area which is small relative to the flow area of blood vessel 24 so as to minimize blood flow restriction while providing an adequate catheter fluid transfer capability.

Anchoring wire element 14 can be made of the materials presently used for catheter guide wires, such as braided or wound stainless steel filaments. Various other materials could also be used, including polymers. Moreover, the anchoring element can be of solid core or hollow constriction. In accordance with a principal feature of this invention, anchoring wire 14 is formed in a configuration such that it radially expands to mechanically engage the side walls of blood vessel 24. In the configuration shown in FIGS. 2 through 4, anchoring wire 14 is formed in a multi-turn helical or "pigtail" configuration such that it is in continuous contact with the vessel side walls and defines a clear flow area through the center of the vessel for blood flow. Such a shape can be easily generated by wrapping guide wire stock around a cylindrical mandrel along a helical path. In its free condition, anchoring wire 14 defines a diameter slightly greater than the inside diameter of blood vessel 24, such that when deployed in blood vessel 24, an expansion force is exerted against the blood vessel wall for anchoring purposes. One end of anchoring wire 1 is received within infusion catheter lumen 20 and is bonded thereto so that these elements remain connected.

Introducer catheter 16 is preferably made from a relatively stiff elastomer, for example, surgical Teflon (TM) could be used. Introducer catheter lumen 28 is sufficiently large to enable infusion catheter 12 and anchoring wire 14 to be inserted through it. Due to the stiffness of introducer catheter 16, as anchoring wire 14 is pulled to retract within lumen 28, it assumes a nearly straightened or "streamlined" configuration, as compared with the expanded state as shown in FIG. 2. The condition of FIG. 1 exists during insertion or withdrawal of the system.

Guide wire 18 is an optional element and is shown inserted within infusion catheter lumen 20 for purposes of stiffening that catheter. As explained in more detail as follows, guide wire 18 facilitates withdrawing introducer catheter 16 while the outer elements remain in position.

Figure 1:
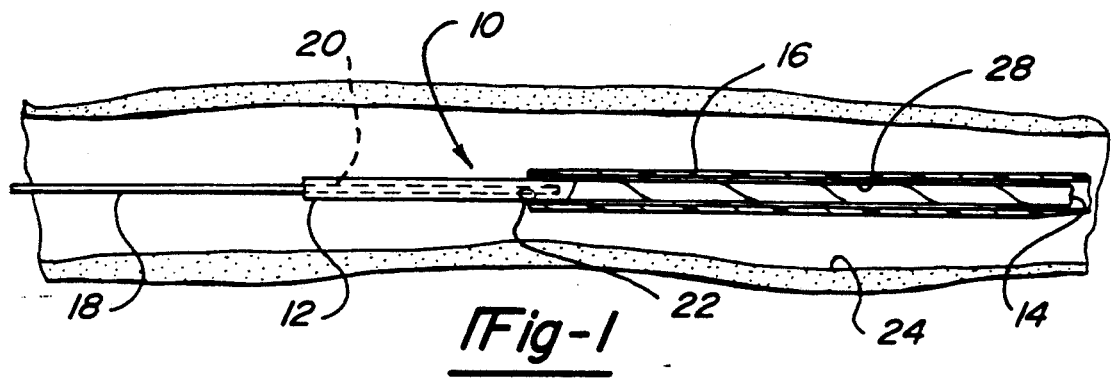
FIG. 1 is a pictorial view of a vascular catheterization system in accordance with a first embodiment of this invention shown with the anchoring element retracted enabling insertion into a blood vessel with the various elements of the embodiment cut-away at the left-hand side of the Figures.
Figure 2:
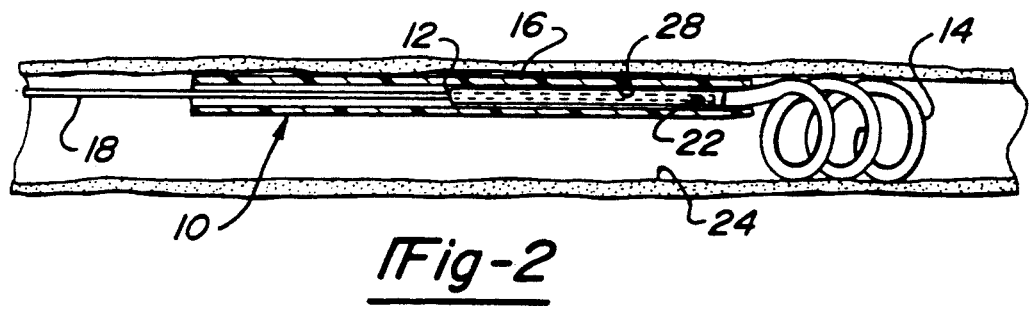
FIG. 2 is a pictorial view of the catheterization system as shown in to FIG. 1 but showing the introducer catheter partly withdrawn, allowing the anchoring element to expand into engagement with the blood vessel wall.

For insertion, the above described elements are assembled in a manner illustrated in FIG. 1, with anchoring element 14 retracted inside introducer catheter 16. Once infusion catheter 12 is properly positioned within the patient, anchoring is achieved by retracting introducer catheter 16 as shown in FIG. 2, allowing anchoring element 14 to expand into engagement with blood vessel 24. Such retraction occurs by restraining infusion catheter 12 outside the patient, while pulling on introducer catheter 16. Since infusion catheter 12 is likely of a type having very little column stiffness, guide wire 18 is fed through lumen 20 until it butts into anchoring wire 14 for stiffening catheter 12.

Figure 3:
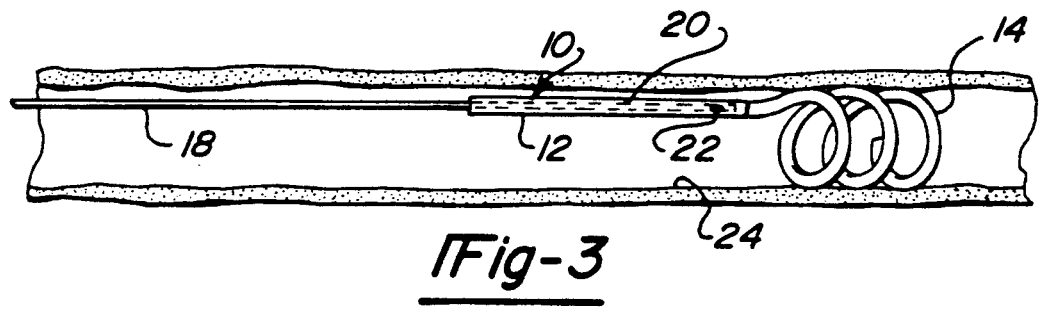
FIG. 3 is a pictorial view showing the catheterization system of FIG. 1 shown with the introducer catheter completely removed.
Figure 4:
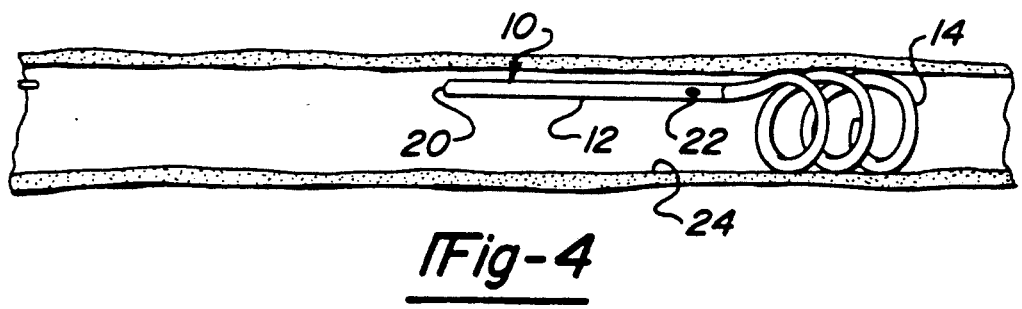
FIG. 4 is similar to FIG. 3 except showing the internal guide wire removed, enabling the infusion or withdrawal of fluids through the implanted catheter.

FIG. 3 shows introducer catheter 16 completely removed and FIG. 4 shows the final step of removing guide wire 18. In this condition, infusion or withdrawal of fluids is permitted through port 22. It should be noted that the helical configuration of anchoring element 14 provides a minimal restriction to the flow of blood through blood vessel 24, since it lies along the inside wall surface of the blood vessel. The presence of anchoring element 14 does, however, induce a degree of turbulence in blood flowing across it. This turbulence is desirable in that it promotes mixing of introduced fluids such as drugs. It is possible to further enhance the mixing feature of forming the anchoring element to protrude into the central region of the blood vessel.

It is highly likely that after a period of time (e.g. several days or weeks) anchoring wire 14 will become embedded within the blood vessel through the process of endothelialization. However, if movement or removal of anchoring wire 14 is desired soon after implantation, infusion catheter 12 may be pulled directly, or anchoring wire 14 can be retracted within introducer catheter 16 by following the procedural steps in the reverse order of that described above for implantation.

Figure 5:
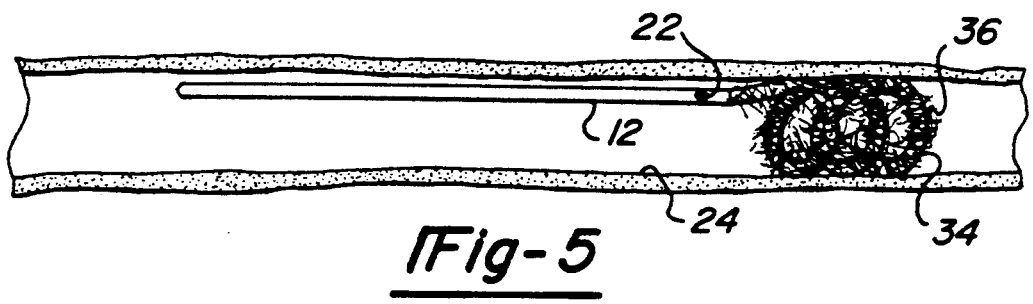
FIG. 5 is a partial pictorial view of a second embodiment of an anchoring element similar to that shown in FIGS. 1 through 4, but having filaments for the purpose of inducing clotting for occluding a blood vessel.

FIG. 5 illustrates elements of a catheterization system in accordance with a second embodiment of this invention incorporating a modified anchoring element designated by reference number 34. This modified catheterization system, like additional embodiments which will be described as follows, includes elements which are identical to those previously described and are accordingly identified by the same reference numbers. Anchoring wire element 34 is identical to anchoring element wire 14 with the exception that numerous filaments of a textile material or "fuzz" is added. Filament material 36 is provided to cause the blood vessel 24, in the anchoring area, to become occluded due to blood clotting. Blood accumulates at filament material 36 and responds by generating a clot. Such an anchoring wire 34 would be employed where such clotting is desired, for example, to control access of drugs to a specific infusion site.

Figure 6:
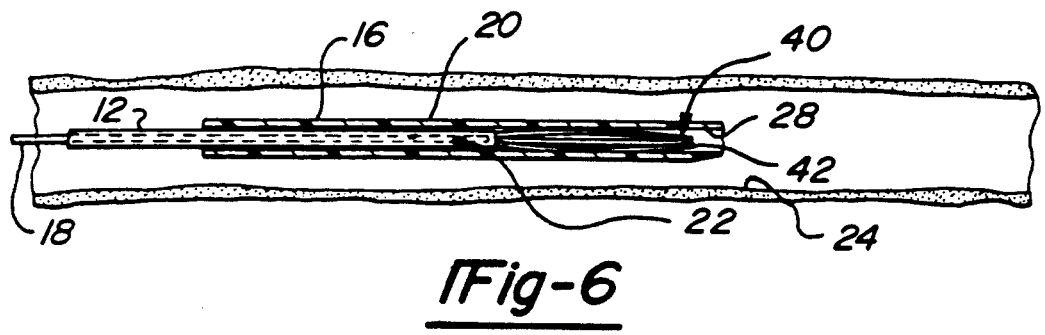
FIG. 6 is a pictorial view of a catheterization system according to a third embodiment of this invention in which the anchoring element includes plural cantilever supported resilient legs.
Figure 7:
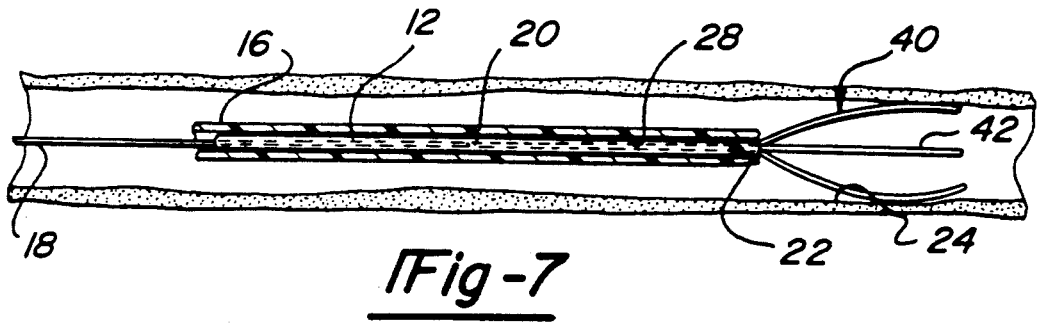
FIG. 7 is a pictorial view of the system of FIG. 6 except showing the introducer catheter partially withdrawn allowing the anchoring element to expand into engagement with the blood vessel.

FIG. 6 illustrates an catheterization system having an anchoring element 40 in accordance with a third embodiment of this invention. In this embodiment, anchoring wire element 14 is replaced by anchoring element 40 having three resilient cantilever supported extending legs 42. Legs 42 are preferably made of round or flat metal stock of a bio-compatible material. Legs 42 in an undeformed condition are separated or expanded sufficiently to engage blood vessel wall 24. Legs 42 are further affixed to infusion catheter 12. FIG. 6 shows anchoring element 40 compressed as it is held within introducer catheter 16. As shown in FIG. 7, once introducer catheter 16 is retracted as in the first embodiment, legs 42 are permitted to expand to engage blood vessel 24. In other respects, this embodiment operates as described for the first embodiment. Although anchoring element 40 is shown having three legs, alternate embodiments could incorporate a greater or smaller number of legs. In fact, a design featuring a single leg would be operable through engaging the blood vessel wall 24 causing the infusion catheter to be forced against the blood vessel wall at a diametrically opposite position.

Figure 8:
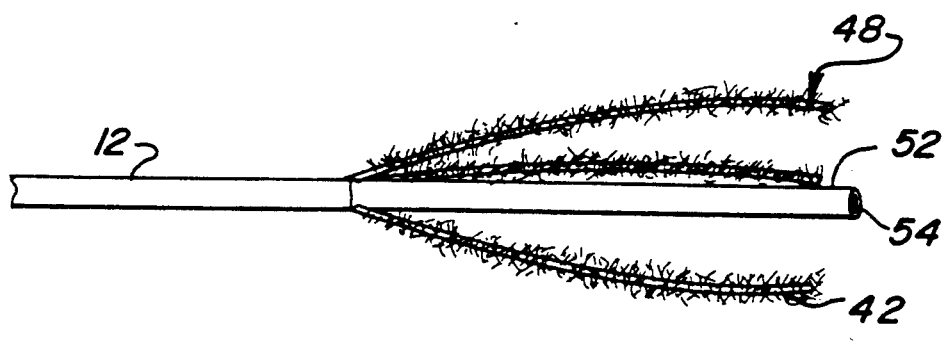
FIG. 8 shows a fourth embodiment of a catheterization system having an anchoring element similar to that of the third embodiment, but including an infusion tube to allow fluid communication beyond the anchoring element and further showing the anchoring element including filaments for inducing clotting.

FIG. 8 is a partial view of a fourth embodiment of an anchoring element 48 in which legs 42 identical to those shown in FIGS. 6 and 7 further include filaments or fuzz material shown in FIG. 5. Anchoring element 48 shown in FIG. 8 also incorporates a central rigid infusion tube 52 to which legs 42 are affixed. With this embodiment, side port 22 of infusion catheter 16 is eliminated, and instead, the entry or withdrawal of fluids through infusion catheter 12 occurs through tube end port 54. This configuration enables drugs to be infused, blood removed or filaments to access "beyond" the position of anchoring element 48 where clotting occurs. A practical implementation of the embodiment shown in FIG. 8 will be described with reference to FIGS. 9 and 10.

While an array of surgical procedures can benefit from the use of catheterization systems in accordance with this invention, two particular procedures are described here for purposes for illustration. In FIGS. 9 and 10, a representative organ, in this case a the human liver 58 is shown in posterior-caudad position (i.e. presented in a cephalad at bottom to caudad at top orientation) with a first blood vessel, the common hepatic artery 60, and a branching vessel, the gastroduodenal artery 62. In FIG. 9, an infusion procedure is illustrated in which it is desired to occlude blood flow through common hepatic artery 60 through the use of anchoring element 48 shown in FIG. 8. Using this device, once a clot is induced within common hepatic artery 60, infusion of drugs into liver 58 is provided while flow through artery 62 is not restricted.

FIG. 10 illustrates an infusion procedure in which it is desired to occlude blood flow through gastroduodenal artery 62 while infusing drugs into liver 58. For this procedure, it is preferred to employ anchoring wire 34 shown in FIG. 5 in which side port 22 provides infusion on the same side of the induced clot of infusion catheter 12. As shown in FIG. 10, the catheterization system provides a mechanism for occluding gastroduodenal artery 62 and also infusing drugs into liver 58.

While the above description constitutes the preferred embodiments of the present invention, it will be appreciated that the invention is susceptible of modification, variation and change without departing from the proper scope and fair meaning of the accompanying claims.

We claim:

1. An implantable vascular catheterization system comprising:
    expandable anchoring means for engaging the walls of a blood vessel, said anchoring means having a segment of filament formed in a multi-turn helical coil, and defining a free diameter sufficiently large to engage the inside wall of said blood vessel,
    an access catheter having said anchoring means affixed to said access catheter at one end of said access catheter, said access catheter having at least one lumen with a port for fluid communication between said access catheter lumen and said blood vessel, and
    an introducer catheter having a lumen for receiving said anchoring means and said access catheter, said introducer catheter lumen receiving and constricting said anchoring means to deform said anchoring means to facilitate introduction of said anchoring means and said access catheter, whereby retraction of said introducer catheter from engagement with said anchoring means allows said anchoring means to expand to engage said blood vessel thereby anchoring said access catheter.

2. An implantable vascular catheterization system according to claim 1 wherein said access catheter lumen receives and affixes said filament end and said access catheter defines a side port adjacent to said anchoring means for communication between said access catheter lumen and said blood vessel.

3. An implantable vascular catheterization system according to claim 1 further comprising a guide wire for insertion into said access catheter lumen for stiffening said access catheter for facilitating retraction of said introducer catheter.

4. An implantable vascular catheterization system comprising:
    an anchoring filament formed of a resilient material and formed in a helical coil defining a diameter such that said coil is engageable with the walls of a blood vessel,
    an access catheter affixed to one end of said anchoring filament and having at least one lumen and a passage for communication between said access catheter lumen and said blood vessel positioned adjacent said anchoring filament, and
    an introducer catheter having a lumen for receiving said anchoring filament and said access catheter such that when said anchoring filament is positioned within said introducer catheter lumen, said anchoring filament is deformed to a generally straightened condition for enabling insertion of said anchoring filament into said blood vessel, and whereby retraction of said introducer catheter from engagement with said anchoring filament allows said anchoring filament to assume said helical configuration thereby engaging said blood vessel and anchoring said access catheter.

5. An implantable vascular catheterization system according to claim 4 wherein said access catheter lumen receives and affixes said filament end and said access catheter defines a side port adjacent said anchoring filament for communication between said access catheter lumen and said blood vessel.

6. An implantable vascular catheterization system according to claim 4 wherein said anchoring filament includes clotting means for causing blood to clot at said filament thereby occluding said blood vessel.

7. An implantable vascular catheterization system according to claim 6 wherein said clotting means comprises a multiplicity of fibers attached to said anchoring filament.

8. An implantable vascular catheterization system according to claim 4 further comprising a guide wire for insertion into said access catheter lumen for stiffening said access catheter for facilitating retraction of said introducer catheter.

9. An implantable vascular catheterization system comprising:
expandable anchoring means for engaging the walls of a blood vessel in the form of a segment of filament formed in a multi-turn helical coil and having an end affixed to said access catheter and defining a free diameter sufficiently large to engage the inside wall of said blood vessel,
an access catheter having said anchoring means affixed to said access catheter and positioned adjacent one of said access catheter, said access catheter having at least one lumen wherein said access catheter lumen receives and affixes said filament end and said access catheter defines a side port adjacent to said anchoring means for communication between said access catheter lumen and said blood vessel, and
an introducer catheter having a lumen for receiving said anchoring means and said access catheter, said introducer catheter lumen receiving said anchoring means to deform said anchoring means to facilitate introduction of said anchoring means and said access catheter, whereby retraction of said introducer catheter rom engagement with said anchoring means allows said anchoring means to expand to engage said blood vessel thereby anchoring said access catheter.

10. An implantable vascular catheterization system comprising:
expandable anchoring means for engaging the walls of a blood vessel, said anchoring means including clotting means for causing blood to clot at said anchoring means thereby occluding said blood vessel,
an access catheter having said anchoring means affixed to said access catheter and positioned adjacent one end of said access catheter, said access catheter having at least one lumen, and
an introducer catheter having a lumen for receiving said anchoring means and said access catheter, said introducer catheter lumen receiving and anchoring means to deform said anchoring means to facilitate introduction of said anchoring means and said access catheter, whereby retraction of said introducer catheter from engagement with said anchoring means allows said anchoring means to expand to engage said blood vessel thereby anchoring said access catheter.

11. An implantable vascular catheterization system according to claim 10 wherein said anchoring means comprises at least one resilient leg element which cooperates to engage said blood vessel and is deflected upon retraction into said introducer catheter lumen.

12. An implantable vascular catheterization system according to claim 10 wherein said clotting means comprises a multiplicity of filaments attached to said anchoring means.

13. An implantable vascular catheterization system comprising:
an anchoring element having at least one elongated resilient leg formed such that said leg is engageable with the wall of a blood vessel, said anchoring element including clotting means for causing blood to clot at said anchoring element thereby occluding said blood vessel,
an access catheter affixed to one end of said anchoring element and having at least one lumen and having a passage for communication between said access catheter lumen and said blood vessel, and
an introducer catheter having a lumen receiving said anchoring element and said access catheter such that when said anchoring element is positioned within said introducer catheter lumen, said anchoring element leg is deformed for enabling insertion of said anchoring element into said blood vessel, and whereby retraction of said introducer catheter from engagement with said anchoring element allows said anchoring element leg to engage said blood vessel thereby anchoring said access catheter.

14. An implantable vascular catheterization system according to claim 13 wherein said clotting means comprises a multiplicity of fibers attached to said anchoring element.

15. An implantable vascular catheterization system comprising:
expandable anchoring means for engaging the walls of a blood vessel,
an access catheter having said anchoring means affixed to said access catheter at one end of said access catheter, said access catheter having at least one lumen with a port for fluid communication between said access catheter lumen and said blood vessel,
an introducer catheter having a lumen for receiving said anchoring means and said access catheter, said introducer catheter lumen receiving and constricting said anchoring means to deform said anchoring means to facilitate introduction of said anchoring means and said access catheter, whereby retraction of said introducer catheter from engagement with said anchoring means allows said anchoring means to expand to engage said blood vessel thereby anchoring said access catheter, and
a hollow tube having a first end communicating with said access catheter lumen and extending beyond said anchoring means whereby a second opposite end of said tube is open to communicate with said blood vessel.

16. An implantable vascular catheterization system comprising:
an anchoring element having at least one elongated resilient leg formed such that said leg is engageable with the wall of a blood vessel,
an access catheter affixed to one end of said anchoring element and having at least one lumen and having a passage for communication between said access catheter lumen and said blood vessel,
a hollow tube, to which said leg is affixed, having a first end communicating with said access catheter lumen and extending beyond said anchoring element whereby a second opposite end of said tube is open to communicate with said blood vessel, and
an introducer catheter having a lumen receiving said anchoring element and said access catheter such that when said anchoring element is positioned within said introducer catheter lumen, said anchoring element leg is constricted and deformed for enabling insertion of said anchoring element into said blood vessel, and whereby retraction of said introducer catheter from engagement with said anchoring element allows said anchoring element leg to engage said blood vessel thereby anchoring said access catheter.

* * * * *

UNITED STATES PATENT AND TRADEMARK OFFICE
CERTIFICATE OF CORRECTION

PATENT NO. : 5,256,146
DATED : October 26, 1993
INVENTOR(S) : William D. Ensminger et al.

It is certified that error appears in the above-indentified patent and that said Letters Patent is hereby corrected as shown below:

Column 5, Line 67, Claim 1, after "coil" insert --having an end--.

Column 7, Line 13, Claim 9, after "one" insert --end--.

Column 7, Line 26, Claim 9, after "catheter" delete "rom" and insert --from--.

Column 7, Line 42, Claim 10, after "receiving" delete "and" and insert --said--.

Signed and Sealed this

Twenty-second Day of February, 1994

Attest:

BRUCE LEHMAN

*Attesting Officer*     *Commissioner of Patents and Trademarks*